(12) United States Patent
Amato

(10) Patent No.: US 7,909,610 B1
(45) Date of Patent: Mar. 22, 2011

(54) COMPUTER-AIDED SYSTEM OF ORTHOPEDIC SURGERY

(75) Inventor: Cyrus J. Amato, Califon, NJ (US)

(73) Assignee: Amato Craniofacial Engineering, LLC, Califon, NJ (US)

( * ) Notice: Subject to any disclaimer, the term of this patent is extended or adjusted under 35 U.S.C. 154(b) by 727 days.

(21) Appl. No.: 12/004,542

(22) Filed: Dec. 20, 2007

Related U.S. Application Data

(60) Provisional application No. 60/871,441, filed on Dec. 21, 2006, provisional application No. 60/885,570, filed on Jan. 18, 2007, provisional application No. 60/899,441, filed on Feb. 6, 2007.

(51) Int. Cl.
G09B 23/28 (2006.01)

(52) U.S. Cl. .......................... 434/270; 434/274

(58) Field of Classification Search .......... 434/262, 434/263, 264, 267, 270, 274, 100
See application file for complete search history.

(56) References Cited

U.S. PATENT DOCUMENTS

| | | | | |
|---|---|---|---|---|
| 1,586,739 A | | 2/1921 | Hanau | |
| 3,802,096 A | * | 4/1974 | Matern | 434/270 |
| 4,200,996 A | * | 5/1980 | Richards | 434/264 |
| 4,541,807 A | * | 9/1985 | Rolfs | 434/264 |
| 4,708,836 A | * | 11/1987 | Gain et al. | 264/40.1 |
| 4,948,373 A | * | 8/1990 | Engels | 434/270 |
| 5,090,910 A | * | 2/1992 | Narlo | 434/82 |
| 5,320,535 A | * | 6/1994 | Min | 434/100 |
| 5,342,202 A | * | 8/1994 | Deshayes | 434/270 |
| 5,720,612 A | | 2/1998 | Shih | |
| 6,112,109 A | | 8/2000 | D'Urso | |
| 6,582,232 B1 | * | 6/2003 | Ney | 434/270 |
| 6,701,174 B1 | | 3/2004 | Krause et al. | |
| 6,978,188 B1 | | 12/2005 | Christensen | |
| 7,731,499 B2 | * | 6/2010 | Sze et al. | 434/270 |
| 2003/0186203 A1 | * | 10/2003 | Aboud | 434/262 |
| 2005/0043835 A1 | | 2/2005 | Christensen | |
| 2005/0133955 A1 | | 6/2005 | Christensen | |
| 2008/0070212 A1 | * | 3/2008 | Haberl | 434/262 |

OTHER PUBLICATIONS

Cheung et al. "Vector Guidance Splint for Internal Maxillary Distraction." J. Oral Maxillofacial Surgery. 2007, pp. 1852-1856. American Association of Oral and Maxillofacial Surgeons.
Sam-Prazisiionstechnik GMBH. Specification sheet for "SAM Transfer System AX." Gauting, Germany, date unknown.
Knezovic-Zlataric et al. "Setting Procedure of the Fully Adjustable SAM 3 Articulator." Acta Stomatol Croat. 2003, 37:3, pp. 283-286.
U. of Texas Dental Branch, "Hanau 'Model C' Articulator." Articulator Archives. 2007.

(Continued)

*Primary Examiner* — Kurt Fernstrom
(74) *Attorney, Agent, or Firm* — Siegmar Silber, Esq.

(57) ABSTRACT

A computer aided system of orthopedic surgery is disclosed and omnidirectional osteogenesis is provided as an example thereof. To perform this surgery a craniofacial anatomic surgical simulator (CASS) is described, in which simulator a stereolithographic medical model is mounted. The medical model hereof is modified for this purpose so that pre-operative intra-oral devices, including custom-fitted fixation plates, can be crafted. An occlusal splint formed on the stereolithographic model acts as an armature for a docking bar which is, during the surgical operation, rigidly affixed to the fixation plate(s). The CASS, in one embodiment hereof, includes an indexing means for alignment of the stereolithographic model. The CASS also simulates the temporomandibular joint and fixedly mounts segments of the model in a post-operative condition.

20 Claims, 3 Drawing Sheets

OTHER PUBLICATIONS

Sinn et al. "Stereolithography for Craniofacial Surgery." J Craniofacial Surgerry. 2006, 17:5, pp. 869-875.

Ellis, Edward. "Accuracy of Model Surgery: Evaluation of an Old Technique and Introduction of a New One." J Oral Maxillofacial Surgery. 1990, 41, pp. 1161-1167. American Association of Oral and Maxillofacial Surgeons.

* cited by examiner

COMPUTER-AIDED SYSTEM OF ORTHOPEDIC SURGERY

CROSS REFERENCE TO RELATED

This is a non-provisional of Provisional Application No. 60/871,441 filed Dec. 21, 2006, entitled Articulator for Patient Generated CAT Scan Craniofacial Stereolith Model; of Provisional Application 60/885,570 filed Jan. 18, 2007 entitled Craniofacial Maxillary Custom Intra-Oral Distraction Device; and of Provisional Application 60/899,441 filed Feb. 6, 2007, entitled Intra-Oral Mandibular Distraction Device, said provisional applications incorporated herein by reference.

BACKGROUND OF THE INVENTION

1. Field of Invention

The present invention relates to methods, devices, and computer generated models for a system of orthopedic surgery and more particularly for surgical employment of distraction osteogenesis using intra-oral omnidirectional distraction devices. This invention is implemented using medical imaging; medical modeling; computer-aided design and manufacturing; a novel craniofacial anatomic surgical simulator, a custom-fitted, removable fixation device with distractor; and, a precision docking mechanism that allows omnidirectional positioning of skeletal segments.

2. Description of the Related Art

In the past, computerization for surgical preplanning purposes has provided stereolithographic models of the anatomic site. These are three-dimensional models constructed using digitized information from scanning devices such as laser and acoustic reflection apparatus and various types of transmission apparatus including X-ray, magnetic resonance imaging (MRI), positron emission (PET or SPECT) as well as ultrasonic radiation.

Upon data being captured by scanning a series of spaced parallel planes, the scans are combinable by computed-tomographic (CT) techniques to construct a three dimensional projection of the scan in the form of a medical model such as a stereolithographic representation. Anatomical modeling using CT-scan data is well known and is widely accepted in pre-operative planning, rehearsal of surgical procedures, and the manufacture of prosthetic devices.

U.S. Pat. No. 6,112,109 of D'urso and U.S. Patent Application Publication 2005/0133955 both describe the use of CT-scan data for constructing prosthetic devices that are custom-fit to provide a better relationship between the remaining healthy bone and the orthopedic implant.

To implement the inventor's system of orthopedic surgery several heretofore unknown devices needed to be developed. A craniofacial anatomic surgical simulator is described, infra, for mounting and working the stereolithographic model. As background to this development, Krause et al. in U.S. Pat. No. 6,701,174 comment that in the complex area of bone distraction surgery "it is difficult, if not impossible, to make accurate surgical plans based solely on a limited number of two-dimensional renderings of bone geometry. This is because of the complex and inherently three-dimensional nature of bone deformities as well as of fixator geometry. Furthermore, two-dimensional depictions of surgical plans may not accurately portray the complexities involved in accessing the target positions of the osteotome and fixator pins surrounding the operated bone. Lack of three-dimensional modeling of these geometric complexities makes it difficult to accurately mount the fixator on the patient according to the presurgical plan".

The computer-assisted preplanning of Krause et al. made an early attempt to resolve this long-felt need through the use of a Taylor Spatial Frame—a collection of fixator struts and associated software; however, they found that the apparatus did not provide visual feedback on how the fixator frame and bone fragments should be moved over time.

As further background to the surgical simulator hereof, in the medical literature Cheung et al. In a 2007 article entitled, *Vector Guidance Splint for Internal Maxillary Distraction* (IL Oral Maxillofacial Surgery, pp. 1852 et seq.) reports using a Hanau Engineering Articulator, developed in the 1920's.

Taking dental articulators as the forebears of the Craniofacial Anatomic Surgical Simulator hereof leads one to view the articulator patent art starting with Hanau, U.S. Pat. No. 1,586,739 and leading patents to Tradowsky, U.S. Pat. No. 4,365,955; El Hadary, U.S. Pat. No. 5,073,109; Federici, U.S. Pat. No. 5,533,896; and Shih, U.S. Pat. No. 5,720,612. None of these devices fulfill the simulation requirements of the disclosure at hand.

SUMMARY

This disclosure describes a craniofacial anatomic surgical simulator (CASS) for mounting a medical model such as a stereolithographic medical model. The framework of the CASS includes a fixed base and a pair of columns arising therefrom, which columns are adjustable to raise and lower a mounting plate on which the craniomaxillary portion of the medical model is mounted. The CASS also provides fixtures to mount the mandibular portion within the glenoid fossae and simulates the temperomandibular joint. The CASS facilitates the formation of pre-operative intra-oral devices required for omnidirectional distraction osteogenesis.

The description of the preferred embodiments, infra, describes two models of the CASS which differ in the manner in which segmented portions of the medical model are held in place. Both describe mounting mandibular portions with three degrees of freedom. In the first embodiment this is accomplished with a movable base for mandibular mounting and in the second embodiment manipulators or "helping hands" are used in place thereof. It is further noted that the medical model is specific to the application at hand in that the truncated upper portion is replaced with a cranial mounting plate. Also, mounting nodes or connectors are placed about the medical model and the CASS framework to facilitate management of the medical model.

The CASS is constructed to enhance the measurement of cephalometric points by providing a grid on the fixed base. Additionally the stereolithographic model may be indexed within the CASS framework by having a computer generated midline reproduced on the cranial mounting plate of a model and matched to a similar midline of the upper mounting plate. Other details of the construct are described in the specification which follows.

OBJECTS AND FEATURES OF THE INVENTION

It is an object of the present invention to provide for pre-fitting or custom fabrication of internal devices for omnidirectional distraction, such as, for craniofacial surgery intra-oral distractors, docking bars, and modified occlusal splints.

It is another object of the present invention to provide a medical model, such as a computed tomographic (CT) generated stereolithographic facial skeleton, to optimize planning and preparation phase of craniofacial surgery.

It is yet another object of the present invention to provide a computer-aided system of surgery whereby through simulation information is gained as to anatomic variables, including the contour and surface mapping of the bone, the quality of the bone, and the location of neurovascular structures.

It is a further object of the present invention to provide in the pre-planning phase the most favorable osteotomy and ostectomy design and the analysis of possible anatomical interferences upon segmental movement.

It is yet another object of the present invention to provide a medical model suitable for mounting in an craniofacial anatomic surgical simulator therefor and facilitating the pre-fitting of internal devices.

It is a feature of the present invention that the craniofacial anatomic surgical simulator hereof has a medical model mounting arrangement with an accurate and functional temperomandibular joint for suitably positioning the maxillofacial and mandibular segments so as to enhance surgical planning.

It is another feature of the present invention that the omnidirectional distraction with the anatomically contoured fixation plates prevents the difficulties of prior intra-oral devices which resulted in the undesired rotation of the maxilla.

Other objects and features of the invention will become apparent upon review of the drawings and the detailed description.

BRIEF DESCRIPTION OF THE DRAWINGS

The invention is described in more detail below with reference to the embodiments shown in the drawing in which like elements are labeled similarly.

DESCRIPTION OF THE PREFERRED EMBODIMENTS

This disclosure describes a new system of orthopedic surgery, which changes present-day craniofacial procedures and is particularly applicable to distraction osteogenesis. In order to work within this new surgical milieu, an initial trio of inventions were required. While the following introductory discussion uses distraction osteogenesis as exemplary, it should be borne in mind that certain devices, such as the craniofacial anatomic surgical simulator (CASS), may be more broadly applied.

Surgical Preplanning

Figure 1:
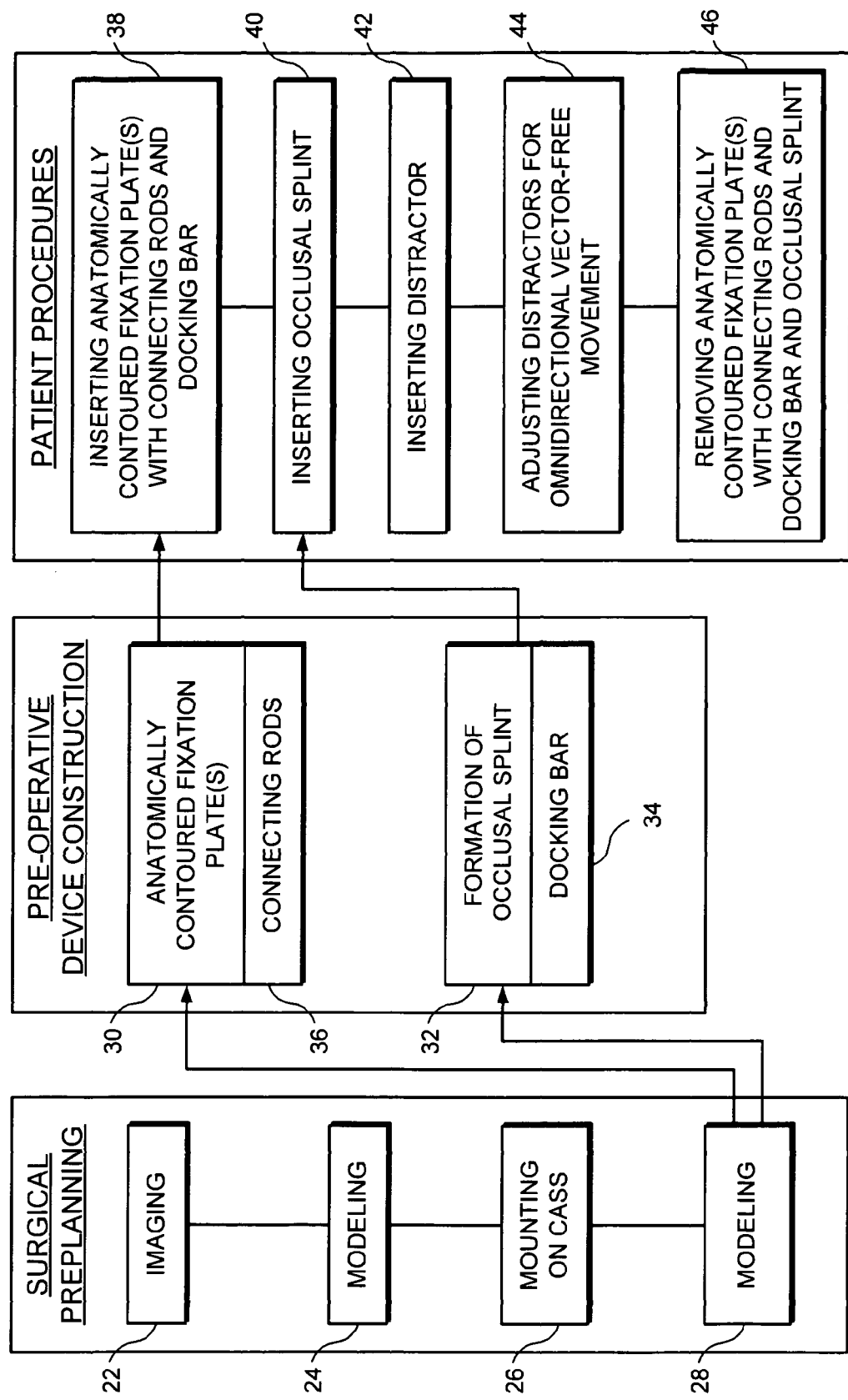
FIG. 1 is a schematic diagram of the new system of orthopedic surgery for which the craniofacial anatomic surgical simulator is designed.

Referring to the schematic diagram of the system FIG. 1, a general overview of the new system of orthopedic surgery is now provided. Three principal divisions are apparent, namely, (1) surgical preplanning; (2) pre-operative device construction; and, (3) patient procedures.

Upon initializing the process, an IMAGING 22 of the patient is first undertaken. The IMAGING 22 step may obtain digitized data from scans of magnetic resonance imaging (MRI), X-ray, computed tomography (CT), ultrasound, laser interferometry or position emission technique (PET). From the collected data, accurate anatomic information as to the bone formation and bone malformation is available.

A medical model, preferably stereolithographic, is formed using MODELING 24 techniques presently extant. Typical of the available modeling techniques are those described in a Christensen, U.S. Patent Application Publication 2005/0133955 for custom prosthesis development. In preparation for the mounting of the model on the craniofacial anatomic surgical simulator which follows, the segments of the stereolithographic model are carefully evaluated.

The inventor's craniofacial anatomic surgical simulator, described in detail herebelow, is now used to mount the parts of the stereolithographic model in the pre-operative positions thereof. The MOUNTING ON CASS 26 process is key to the extreme accuracy of the omnidirectional distraction. The MOUNTING ON CASS 26 process provides the facility for accurately forming the docking bar and the surface mapping required for the anatomically contoured fixation plates and the process does so without the need for vector determination or vector guides.

The mounted stereolithographic medical model also provides, during surgical preplanning, for the SIMULATING 28 phase. Here any osteotomy required and the incisions for installing the custom-fitted fixation plates are preplanned. Upon receipt of the customized contoured anchor from the laboratory, the casting is fitted to the model and, with the docking bar in place, the day-to-day distraction movement and adjustment is planned.

Pre-Operative Device Construction

Using omnidirectional distraction osteogenesis as an example, the surgeon, either alone or with the support team, forms a wax model for lost-wax casting of ANATOMICALLY CONTOURED FIXATION PLATES device 30. In the example described below, the medical model, being an accurate representation of the cranial skeletal structure, custom fits the ANATOMICALLY CONTOURED FIXATION PLATES 30 so as to follow the surface map of the bone contours at the site of installation. In this manner, the device is pre-operatively precision fitted to the patient and, unlike some prior art intra-oral devices, does not require bending at the time of installation. Besides the preciseness of custom-fitting and the removal of the bending requirement, the ANATOMICALLY CONTOURED FIXATION PLATES 30 are rigid devices which eliminate vector requirements, including vector alignment and vector guides.

Again using omnidirectional distraction osteogenesis as an example, the surgeon either alone or with the support team, places all the segments of the stereolithographic model in the post-operative position and forms an OCCLUSAL SPLINT/DOCKING BAR ARMATURE 32. With the segments of the model assembled on the CASS in the final position to be attained, the preforming of the DOCKING BAR 34 and designing and forming of the CONNECTING RODS 36 completes the pre-operative device construction. These devices enable the surgical procedure in which full distraction in all directions becomes feasible.

Patient Procedures

Referring again to FIG. 1, the operative steps are now described. First, the step of inserting the devices fabricated pre-operatively is completed. The INSERTING ANATOMICALLY CONTOURED FIXATION PLATE(S) WITH CONNECTING RODS AND DOCKING BAR 28 is accomplished with the ends of the fixation plates anchoring the plates by wrapping around and undercutting the bones at the installation sites. The occlusal splint upon which the docking bar 34 was formed is inserted at INSERTING OCCLUSAL SPLINT 40.

With this accomplished, a distractor, such as a Dynaform distractor (as manufactured by Stryker Leibinger BmbH &

Co., Freiburg, Germany) is employed, and emplaced on the docking bar at INSTALLING DISTRACTOR 42.

With the device installation completed, what remains is ADJUSTING DISTRACTORS FOR OMNIDIRECTIONAL VECTOR-FREE MOVEMENT 44 and REMOVING ANATOMICALLY CONTOURED FIXATION PLATE (S) WITH CONNECTING RODS AND DOCKING BAR AND OCCLUSAL SPLINT 46.

Craniofacial Anatomic Surgical Simulator

Figure 2:
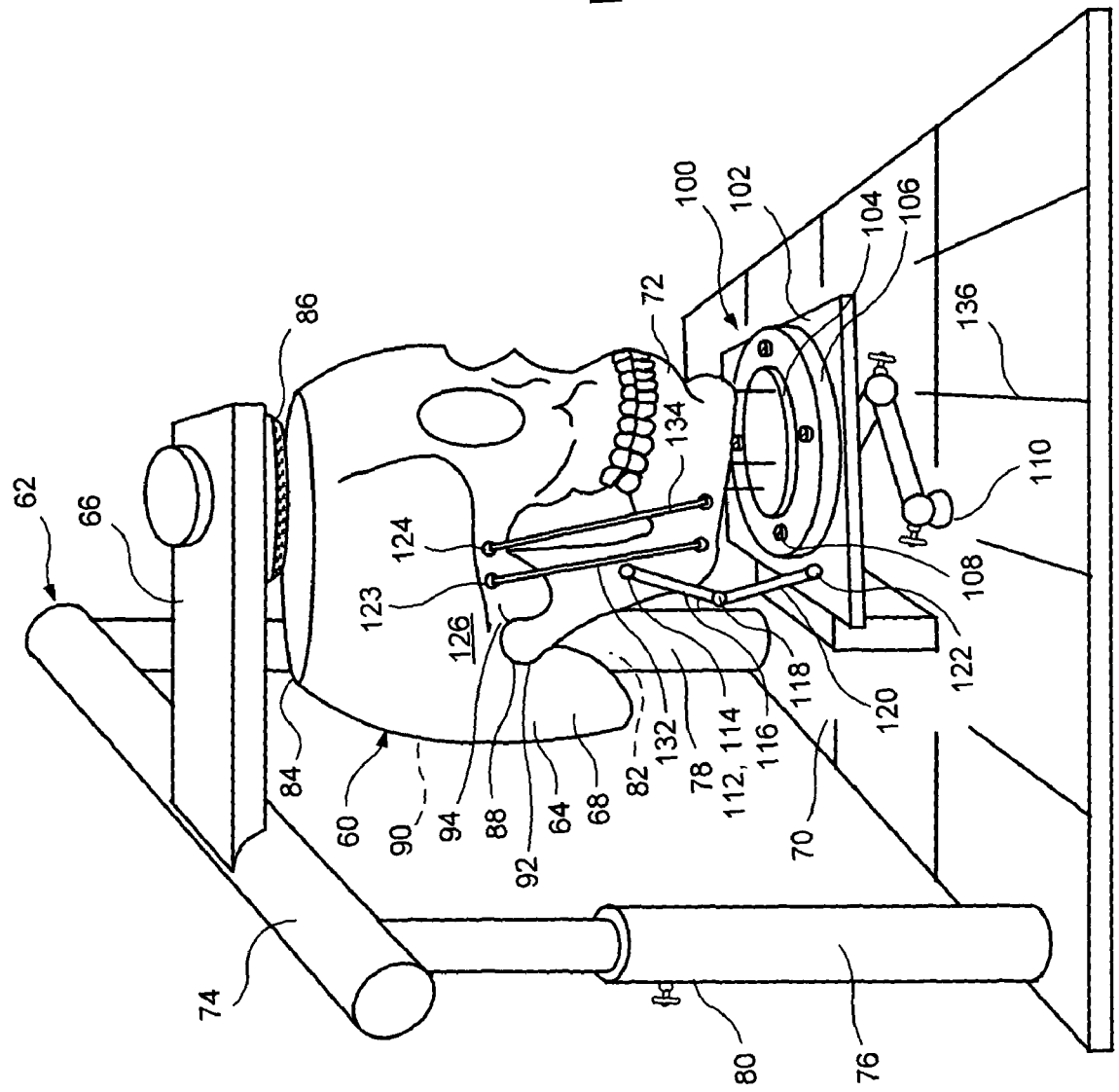
FIG. 2 is a perspective view of the first embodiment of the craniofacial anatomic surgical simulator of this invention having a uniquely positionable mandibular mounting arrangement; and, FIG. 3 is a perspective view of the second embodiment of the craniofacial anatomic surgical simulator of this invention utilizing transfer assemblies to hold segments of the stereolithographic model.
Figure 2:
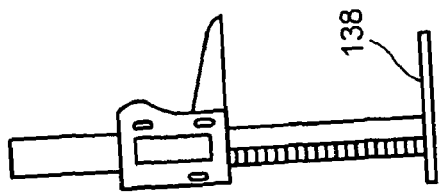

Referring now to FIG. 2, the craniofacial anatomic surgical simulator (CASS) is now described. The CASS is referred to generally by the reference designator 60 and provides a framework 62 for accommodating the stereolith model 64. The framework 62 is constructed with an upper mounting plate 66 for attaching the craniomaxillary portion 68 of the stereolithographic model 64 and a base mounting plate 70 for attaching the mandibular portion 72 of the stereolith model 64.

The framework 62 of the CASS 60 further comprises a crossbar or strut 74 to which the upper mounting plate 66 is connected. While in the present embodiment the strut 74 upper mounting plate 66 is fixed, it is within the contemplation of the present invention that this connection could swivel for right-to-left adjustment or be hinged for forward/back adjustment. The framework 62 of the CASS 60 further comprises adjustable posts or retaining elements 80 and 82 that maintain the upper mounting plate 66 at the selected elevation.

The medical model 64 consisting of the craniomaxillary portion 68 and the mandible or mandibular portion 72 is adapted for mounting on the CASS 60. The craniomaxillary portion 68 is modified for the purpose of the above-described surgery by having the uppermost cranial portion removed and replaced by a cranial attachment plate 84 which is mounted to the upper mounting plate 70 by an adhesive layer 86.

An artificial temporomandibula joint (TMJ) 88 and 90 is constructed to attach the mandible 72 between the base 70 and the craniomaxillary portion 68. As the stereolithographic model 64 does not represent the soft tissue component of the TMJ 88 and 90, the opening in the glenoid fossae 92 is filled with soft resilient dental liner or reline 94 (such as COE-SOFT Resilient Dental Liner manufactured by GC America, Inc., Alsip, Ill. 60803 or equivalent). This enables the mandible 72 to rotate during simulated surgery in an accurate manner.

The mandible 72 is also attached through a mandibular mounting mechanism 100 to the base mounting plate 70. The mounting mechanism 100 is constructed with a mandibular base plate 102 and intermediate plates 104 and 106. In the embodiment shown, plate 106 is attached to mandibular base plate 102 with three positioning screws 108 enabling the removal and remounting of the mandible 72 without losing the original location or orientation.

The mandibular mounting mechanism 100 is attached to the base 70 of the CASS 60 with two posts (not shown) and three universal movement lock joints 110. During simulated surgery, this mounting arrangement enables the movement of the mandible 72 vis-á-vis the craniomaxillary portion into the desired post-operative position.

When the CASS 60 is used to simulate mandibular ramus surgery, it is necessary to configure the device so that the proximal segment of the mandibular ramus is fixed. To accomplish this, a ramus pin 112 is disposed on both sides of the stereolith model 64 and a ramus pin lock joint 114, similar to lock joint 110, is secured thereto. Depending from lock joint 114 is upper guide rod 116, which, in turn, is secured to intermediate lock joint 118 and to lower guide rod 120. The lower guide rod 120 is secured to mandibular base plate 102 through base plate lock joint 122. With this structure in place, the mandible 72 relation to the craniomaxillary portion 68 is adjusted by a change in elevation at posts 76 and 78 being locked in place at clamps 80 and 82 and by unlocking the previously described lock joints sliding and rotating the segments to the desired position and locking the joints.

Optionally, at an angle mimicking the massateric sling, on both sides of the stereolithographic model 64, upper pegs 122 and 124 are placed in the zygomatic arch 126 and lower pegs 128 and 130 are placed in the mandible 72 with elastics 132 and 134 therebetween.

In operation the CASS 60 fulfills numerous pre-surgical functions. Specific to craniofacial surgery, the CASS 60, because of its extreme accuracy, facilitates the collection of cephalometric data. This is aided when a grid 136 is provided on base 102 for use in positioning measuring instruments.

Figure 3:
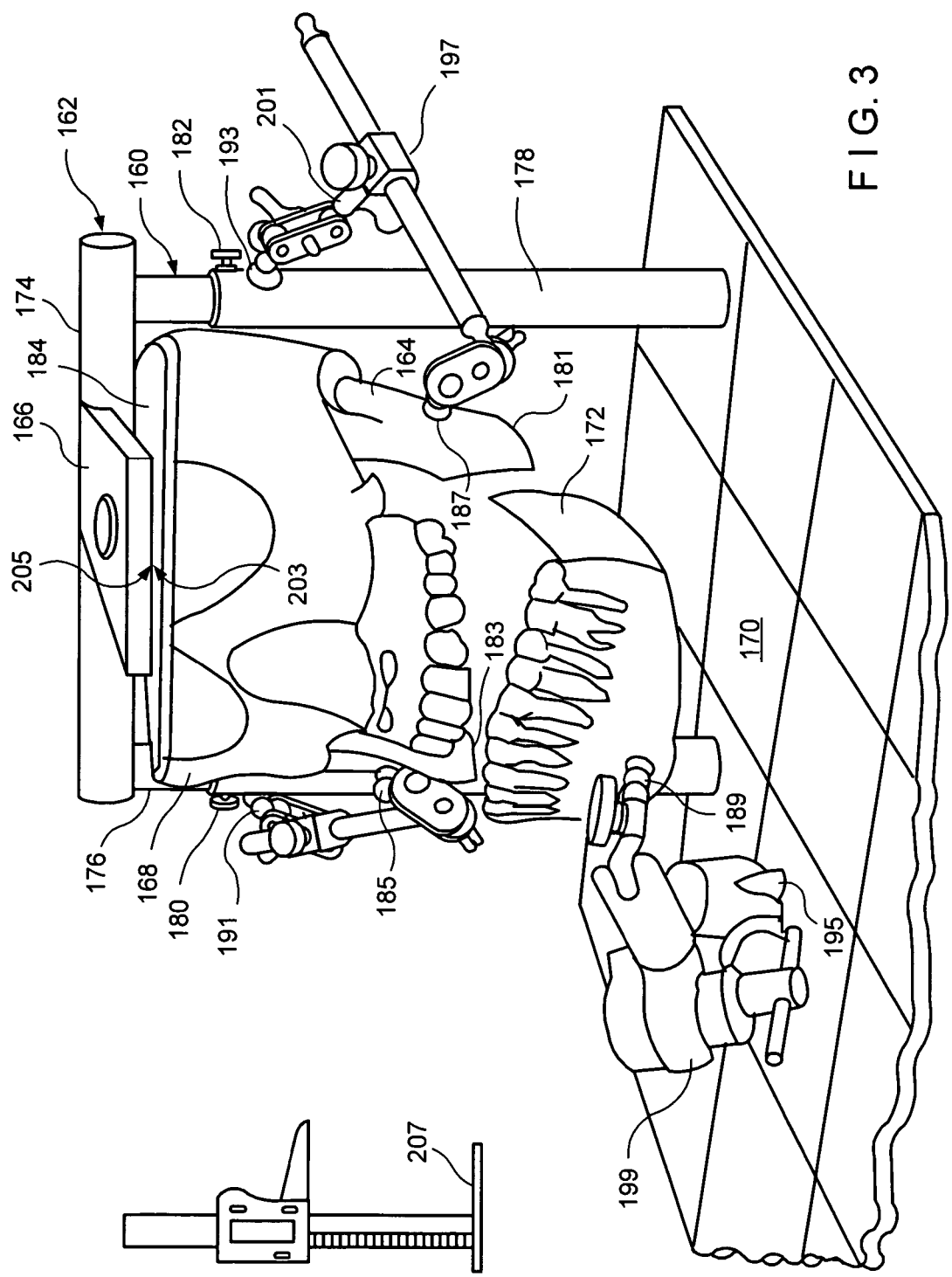

For the craniofacial surgical technique described above, the CASS 60 provides a form for modeling the Referring now to FIG. 3, a second embodiment of the craniofacial anatomic surgical simulator (CASS) is shown and is now described. The CASS device is referred to generally by the reference designator 160. In this embodiment, similar parts to those of the first embodiment are referred to by reference designators 100 units higher than a similar part in the first embodiment.

The CASS device 160 provides a framework 162 for accommodating the stereolithographic model 164. The framework 162 is constructed with an upper mounting plate or extension arm 166. Optionally, the mounting plate 166 is constructed to include a universal swivel joint (not shown) for freely adjusting the same. The upper mounting plate 166 attaches the craniomaxillary portion 168 of the stereolithographic model 164. The framework 162 further includes a base mounting plate 170 for attaching the mandibular portion or mandible 172 of the stereolithographic model 164.

The framework 162 of the CASS 160 further comprises a crossbar or strut 174 to which the upper mounting plate 166 is connected. Adjustable posts 176 and 178 are held by retaining elements 180 and 182 to maintain upper mounting plate 166 at the selected elevation.

As previously mentioned, the stereolithographic model 164 consists of two basic parts, namely, the craniomaxillary portion 168 and mandible 172 is modified slightly differently from that of the first embodiment. Here, at each ramus segment 181 and 183, corresponding male attachment node or ramus connector 185 and 187 is emplaced. Similarly an attachment node or mandible connector 189 is emplaced on mandible 172. For easy management of the stereolithographic model 164, the framework 162 is constructed with a male attachment node or column connector 191 and 193 on each adjustable post 176 and 178, respectively, and at least one base connector 195 on base 170. Between ramus connector 185 and column connector 191, a manipulator or transfer device 197 (such as Kronus Helping Hands Model HD23, Catalog #64-2991, Radio Shack Corporation, Fort Worth, Tex. 76102 or equivalent) holds the ramus segment 181 (which has been separated from mandible 172).

As shown in FIG. 3, a manipulator or transfer device 199 (such as Axiomatic Transfer Fork Assembly Model 050-155 of SAM—Präzisionstechnik Gmble, Gauting, Germany or equivalent) holds the mandibular segment 172 between base connector 195 and mandibular connector 189. Completing the mounting arrangement for the model 164, the ramus segment 183 in a manner analogous to segment 181, is held by a transfer device 201 between ramus connector 187 and column connector 193.

The stereolithographic model 164 is truncated by having the uppermost cranial portion removed and replace by a cranial mounting plate 184. In this embodiment the midlines of the cranial mounting plate 184 and the upper mounting plate 166 form a reference means with, for example, the midline 203 of cranial mounting plate 184 being raised and midline 205 of upper mounting plate 166 being indented. Thus, upon mounting, midline 203 interengages with midline 205 resulting in the positive indexing of stereolithographic model 164 on framework 162.

Because many varying and different embodiments may be made within the scope of the inventive concept herein taught and because many modification may be made in the embodiments herein detailed in accordance with the descriptive requirements of the law, it is to be understood that the details herein are to be interpreted as illustrative and not in a limiting sense.

What is claimed is:

1. An apparatus for mounting craniofacial anatomic components used in surgical simulation comprising:
    a fixed base;
    a pair of columns arising from said base, said columns being of adjustable height;
    a mounting plate cantilevered from said columns, said mounting plate adapted to receive a truncated craniomaxillary portion thereon, said mounting plate with said truncated craniomaxillary portion depending therefrom being raised and lowered upon adjustment of said columns; and,
    manipulator means adapted to receive a mandibular portion thereon, said manipulator means base with said mandibular portion thereon, positionable with three degrees of freedom in relation to said truncated craniomaxillary portion;
    whereby, upon simulation, said anatomic components are moved to post-operative positions providing the requisite surgical planning.

2. An apparatus as described in claim 1 wherein said manipulator means is a movable base disposed on said fixed base.

3. An apparatus as described in claim 2 wherein said movable base further comprises:
    reference means for returning said movable base to original location.

4. An apparatus as described in claim 3 wherein said reference means is a plurality of positioning screws.

5. An apparatus as described in claim 1 wherein said fixed base further comprises:
    a grid thereon adapted for measuring cephalometric points.

6. An apparatus as described in claim 1 further comprising:
    a crossbar disposed on said columns with said mounting plate attached thereto.

7. An apparatus as described in claim 6 wherein said crossbar and said mounting plate have a swivel attaching the one to the other, said swivel adapted for adjustment of said truncated craniomaxillary portion.

8. A craniofacial anatomic surgical simulator (CASS) comprising:
    a mounting apparatus for a stereolithographic model, in turn, comprising:
        a fixed base;
        a pair of columns arising from said base, said columns being of adjustable height;
        a mounting plate cantilevered from said columns, said mounting plate adapted to receive a truncated craniomaxillary portion thereon, said mounting plate with said truncated craniomaxillary portion depending therefrom being raised and lowered upon adjustment of said columns; and,
        manipulator means disposed on said fixed base, adapted to receive a mandibular portion thereon, said manipulator means with said mandibular portion thereon positionable with three degrees of freedom in relation to said truncated craniomaxillary portion;
    a medical model fabricated using computerized tomographic techniques from digitized data, said medical model, in turn, comprising:
        a truncated craniomaxillary portion having the uppermost region removed leaving an opening thereinto;
        a cranial attachment plate at said opening of said truncated craniomaxillary portion, said cranial attachment plate affixed to said mounting plate of said mounting apparatus;
        a mandibular portion; and,
        a glenoid fossae with a simulated soft tissue component therein attached to said truncated craniomaxillary portion.

9. An apparatus as described in claim 8 wherein said movable base further comprises:
    reference means for returning said movable base to original location.

10. An apparatus as described in claim 9 wherein said reference means is a plurality of positioning screws.

11. An apparatus as described in claim 8 wherein said fixed base further comprises:
    a grid thereon adapted for cephalometric techniques.

12. An apparatus as described in claim 8 further comprising:
    a crossbar disposed on said columns with said mounting plate attached thereto.

13. An apparatus as described in claim 12 wherein said crossbar and said mounting plate have a swivel attaching the one to the other, said swivel adapted to provide right-to-left adjustment of said truncated craniomaxillary portion.

14. An apparatus as described in claim 8 wherein said craniomaxillary portion is indexed to said mounting plate using cranial midline data and inscribing the midline on said cranial attachment plate.

15. An apparatus as described in claim 14 wherein said cranial midline is raised and a midline channel is impressed in said mounting plate, said cranial midline engaging said midline channel upon said craniomaxillary portion being mounted thereon.

16. A medical model for simulating craniofacial surgery fabricated using computerized tomography from digitized data, said medical model comprising:
    a truncated craniomaxillary portion having the uppermost region removed leaving an opening thereinto;
    a cranial attachment plate at the said opening of said truncated craniomaxillary portion, said cranial attachment plate adapted for mounting said medical model to a surgical simulator;
    a glenoid fossae with simulated soft tissue component thereon attached to said truncated craniomaxillary portion; and,
    a mandible with the condyle thereof disposed in said glenoid Possa said temporomandibular joint;
    whereby said medical model is mountable in a craniofacial anatomic surgical simulator to demonstrate pre-operative conditions and to simulate surgical procedures.

17. A medical model as described in claim 16 wherein said medical model is a stereolithographic device.

18. A medical model so described in claim 17 wherein said craniofacial surgery includes, in said post-operative conditions, distraction osteogenesis with regenerative growth voids, said medical model further comprises:
- a filler in said regenerative growth voids to simulate said distraction osteogenesis.

19. A medical model as described in claim 16 wherein said cranial attachment plate further comprises:
- indexing means for aligning said craniomaxillary portion, said indexing means disposed on said cranial attachment plate.

20. A medical model as described in claim 19, wherein said craniomaxillary portion is indexed using cranial midline data and inscribing the midline on said cranial attachment plate.

* * * * *